Figure 1:
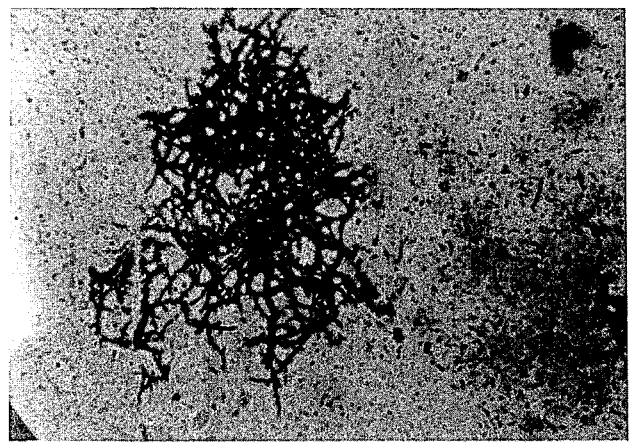

United States Patent [19]
Ward et al.

[11] 3,950,224
[45] Apr. 13, 1976

[54] METHOD FOR CLONING FILAMENTOUS MICROORGANISMS

[75] Inventors: Calvin B. Ward, Kensington; Robert D. Bruner, Richmond, both of Calif.

[73] Assignee: Cetus Corporation, Berkeley, Calif.

[22] Filed: Sept. 3, 1974

[21] Appl. No.: 502,441

[52] U.S. Cl. .................................. 195/76; 195/121
[51] Int. Cl.² ............................................ C12B 1/00
[58] Field of Search ......... 195/81, 121, 1, 104, 108, 195/76, 96, 112

[56] References Cited
OTHER PUBLICATIONS

Davis et al., "Microbiology," Harper & Row Publishers, 1967, pp. 967–968.

Stanier et al., "The Microbial World," Prentice Hall Publishers, Third Edition, 1970, pp. 56–59.

*Primary Examiner*—A. Louis Monacell
*Assistant Examiner*—R. B. Penland
*Attorney, Agent, or Firm*—Fitch, Even, Tabin & Luedeka

[57] ABSTRACT

A method is described for cloning filamentous microorganisms wherein the microorganisms are suspended in a liquid media and fragmented to produce a substantial increase in the number of viable filaments which are less than a predetermined size. Those filaments which are less than the predetermined size are then separated from the balance of the suspension of filaments by filtering.

10 Claims, 3 Drawing Figures

METHOD FOR CLONING FILAMENTOUS MICROORGANISMS

This invention relates generally to the cloning of microorganisms and, more particularly, to the cloning of filamentous microorganisms in order to produce colony-forming units for which the probability is high of the development of a genetically pure colony.

An area of major importance in microbiological research is in the search for new or improved strains of microorganisms for accomplishing various purposes. For example, products of microbial activity are of present or potential importance in the commercial production of alcoholic beverages, foods, acidulents, organic acids, and antibiotics.

Typically, the technique employed in the research for new or improved strains of microorganisms is to culture microorganisms having naturally or artificially induced genetic variations. The metabolic products of these microorganisms, usually after fermentation, are then examined to determine which, if any, of these microorganisms has produced a desired improvement.

A typical initial procedure in the search for new or improved strains of microorganisms involves the growing of colonies of the microorganisms sufficiently large for further study. Ideally, these colonies are genetically pure so that each colony represents a distinct potential variation of the strain or strains under study. In fact, for genetic studies, it is desirable to have each colony-forming unit contain only a single nucleus. Where the microorganism is filamentous, it may be satisfactory if the colony-forming units contain several nuclei if most or all nuclei are genetically identical.

For sporulating microorganisms, even though the vegetative growth may be filamentous, it is usually possible to use a single spore as the colony-forming unit in genetic experiments. Since most spores are presumably uninucleate, it is relatively easy to obtain genetically pure colony-forming units.

Under some circumstances, it may be preferable to carry out the program on growing cells rather than spores. This may be the case with filamentous microorganisms that do not sporulate or sporulate very poorly or have multi-nucleate spores. Moreover, even if the microorganism under study sporulates well, growing cells may be preferred because they may respond better to mutagenesis.

Each colony-forming unit may, therefore, contain many tens or hundreds of nuclei which may or may not be genetically identical. If a filamentous culture is treated with a mutagen to introduce genetic inhomogeneity into the culture, any genetic variations having significantly better productivity in the culture are typically masked. The masking that occurs is inherent in the usual procedure for screening such microorganisms in accordance with known prior art techniques.

More particularly, typical prior art procedures in genetic experiments plate out a filamentous culture on nutrient agar after treating the culture with a mutagen to introduce genetic heterogeneity. After a sufficient period of growth, colonies are selected and used to inoculate individual shake flasks containing nutrient media. Since any one of the original filaments typically contains hundreds of nuclei, the resulting colony from each such filament, and hence the resulting culture which grows in the shake flask, is a mixed culture containing strains of different productivities. Since most mutations are deleterious, a strain resulting from a random mutation of the parental strain will, in general, have a productivity less than or equal to the productivity of the parental strain. Thus, the average productivity measured in each of the shake flasks is normally less than or equal to that of the parental strain. Those few strains which may have significantly better productivity are masked by the averaging process.

Accordingly, it is an object of the present invention to provide an improved method for cloning filamentous microorganisms.

Another object of the invention is to provide a method for growing genetically pure colonies from a population of inhomogeneous filamentous microorganisms.

Still another object of the invention is to provide a method for producing genetically pure colony-forming units for microorganisms such as Micromonospora which grow as large mycelial networks.

Figure 2:
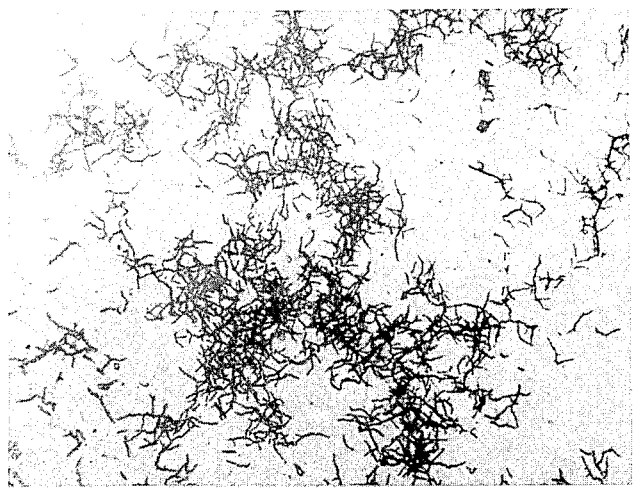
Figure 3:
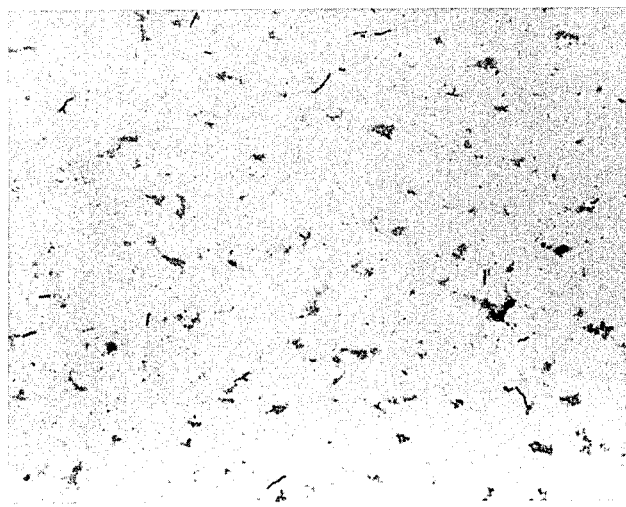

Other objects of the invention will become apparent to those skilled in the art from the following description, taken in connection with the accompanying illustrations wherein:

FIG. 1 is an enlarged photograph of a typical heterogeneous population of filamentous microorganisms in the untreated state;

FIG. 2 is an enlarged photograph of a typical heterogeneous population of filamentous microorganisms after undergoing fragmentation to produce a substantial increase in the number of filaments; and FIG. 3 is an enlarged photograph of a typical heterogeneous population of filamentous microorganisms after filtering through a filter having pores of a size to pass substantially only those filaments having less than a predetermined size.

Very generally, the method of the invention includes suspending the filamentous microorganisms to be cloned in a liquid media. The microorganisms in suspension are fragmented to produce a substantial increase in the number of viable filaments which are less than a predetermined size. Those of the filaments which are less than the predetermined size are then separated from the balance of the suspension of filaments by filtering.

The initial source of the microorganism or microorganisms to be cloned depends upon the particular type of research being conducted. For example, in the search for new types of microorganisms, soil may be an ideal source of microorganism populations of great variety. On the other hand, the cloning problem is usually more acute where a known filamentous microorganism is to be subjected to mutagenesis and subsequently examined for its properties. Although, as will be explained more fully below, the step of effecting mutagenesis may or may not be performed and, if performed at all, may be performed at any of several different points in the process, the basic process of the invention remains the same.

Initially, the culture with which the process of the invention begins should be in a liquid or liquifiable medium. The culture may be grown in a liquid nutrient medium or may be initially grown on a solidified nutrient medium such as nutrient agar, and subsequently removed therefrom and suspended in the liquid medium. In either case, the method of the invention initially contemplates the suspension of the microorganisms to be processed in liquid media.

Assuming the microorganisms to be examined are heterogeneous, that is, are comprised of a wide variety of genetically different strains, the cloning procedure is for the purpose of reducing the large groups of connected nuclei into smaller colony-forming units in which there is a high probability that the nuclei are genetically identical, or in which a single nucleus exists. To this end, the microorganisms suspended in the liquid media are subjected to a fragmentation step to produce an increase in the number of small viable filaments.

The increase in the number of filaments should be substantial, since what is desired is as large a number of viable filaments as possible. It is also desired that each filament be small enough as to possess a likelihood of having all its nuclei identical. Each colony grown from such a filament will, therefore, be genetically pure.

The technique employed for fragmentation may vary depending upon the particular microorganisms being processed. Factors which control the selection of the fragmentation technique include the susceptibility of the microorganism to various fragmentation procedures and the ability of the microorganism to withstand the particular fragmentation technique utilized and remain viable. One particular technique which may be useful is the employment of a homogenizer (e.g. the "Virtis 45" made by Virtis Company, Gardiner, N.Y.). Such a device, under certain conditions, is capable of producing an increase in the number of small viable filaments of *Micromonospora purpurea* of 100-fold or more when operated at top speed for two minutes with cooling. Another technique employed may be the use of glass homogenizing beads along with agitation. Such a technique is capable of producing an increase in the number of small viable filaments of about 20-fold. Other techniques for fragmentation may employ tissue homogenizers, "Waring" blenders, chemical or enzymatic treatment, and ultrasonic irradiation. Although the more violent fragmentation techniques, such as the use of a homogenizer, may provide advantages in some cases, more of the microorganisms may be killed in the process than with less violent techniques.

The results of the fragmentation step may be seen by comparing FIGS. 1 and 2. FIG. 1 represents an unfragmented culture of a typical Micromonospora strain. The long mycelial chains may be observed in FIG. 1. Such chains may contain between 50 and 1000 nuclei. FIG. 2 illustrates the same population after fragmentation in a Vortex mixer. As may be seen, the Micromonospora are readily fragmented by mechanical shear during this procedure, which produces a substantial increase in the number of small filaments.

As may be seen from FIG. 2, the fragmentation produced by the homogenizer is not perfect in that many mycelia remain containing a large number of nuclei. Since it is desirable that each colony-forming unit contain only one or a few nuclei, the fragmented mycelia are subjected to a further step in which those filaments which are less than a predetermined size are selected and separated out from the suspension. This is accomplished by filtering and may also include a preliminary centrifuging. The filter is selected so the size of the fragments passed is such that the passed fragments are likely to have the desired number of nuclei.

Experience has indicated that filters vary considerably in their effectiveness. Of the many commercially available brands of micron range membrane filters, some work well and some do not work and as yet it has not been determined why. Thin filters having pores which are straight and clean usually are effective, but this is not necessarily a requirement. Usually, the pore diameter should be between one and two times the smallest dimension of the microorganism filaments. A smaller size will block all fragments and a larger size will allow longer filaments to fold double and pass through.

For Micromonospora, pore sizes in the range of one micron to about five to six microns are typically satisfactory. Micron range filters which have been successfully used for *Micromonospora purpurea* include a five micron "Mitex" filter (Millipore Corporation, Bedford, Mass.) and 1 micron and 2.1 micron "Nuclepore" filters (Nuclepore Corporation, Pleasanton, Calif.). Nuclepore filters have also been used successfully with *Streptomyces erythreus*. Other filters which have been used successfully with Micromonospora include a "Duralon" filter made by the Millipore Corporation, and an "Acropor" filter made by Gelman Instrument Co., Ann Arbor, Michigan. In each case, a standard syringe filter and filter holder may be used, or non-manual devices such as pneumatically operated filter syringes may also be used.

Under some circumstances, filtering may be difficult, since the suspension being filtered may be excessively thick and clog the filter. If so, a preliminary centrifugation step or cotton prefilter may eliminate the large clogging fragments and facilitate the filtering operation. Naturally, the percentage of the culture which passes through the filter will depend upon the extent of the previous fragmentation step, and the size and nature of the pores in the filter used.

For a particular microorganism, the specific manner in which the method of the invention is carried out depends upon a number of factors. Some microorganisms may be sensitive to the homogenizing step in that over-homogenizing may cause injury and result in an unduly large disparity between the viable count and the cell count. Greater homogenization usually leads to higher density filtrates.

For some microorganisms or for certain purposes, it may be desirable to recycle or repeat certain steps in the method. For example, for mutated microorganisms, after an initial fragmentation step, the population of microorganisms being cloned may be allowed to grow for a while and then may be subjected to a further fragmentation step. Alternatively, the entire cycle may be repeated by first fragmenting, filtering and then refragmenting and refiltering. By using an appropriate intermediate growth period before the recycle, the separated fragments may significantly increase in size (at least double) and may increase the probability that the recycled or double filtered population will contain genetically pure colony-forming units.

In the search for new or improved strains of microorganisms, separation of the microorganisms into genetically pure colony-forming units enables a careful analysis of each unit for its own particular properties. It may be that the research is directed to measuring spontaneous variation, in which case the colony-forming units would not be subjected to mutagenesis. Typically, however, in the search for new strains, such as developing new strains of antibiotic producing microorganisms, the colony-forming units are subjected to mutagenesis at some point or other. The mutagenesis may be effected by means of ultraviolet light, nuclear radiation, or heat, may be chemically induced, or may be induced by other suitable means.

Depending upon the characteristics of the microorganism, the mutagenesis may be introduced at any selected point in the method of the invention. Thus, for example, the initial suspension of microorganisms in the liquid media may be subjected to mutagenesis prior to any fragmenting or separating steps. On the other hand, mutagenesis may be introduced between the fragmenting and separating steps, or after the separation step has occurred. If recycling is used, mutagenesis may be introduced between the initial full cycle and the repeated cycle.

In practicing the method of the invention, it is important to carefully monitor the results of each of the steps. This is conveniently done by microscopy and enables the user of the process of the invention to make whatever parameter adjustments are necessary in the process to ensure satisfactory cloning. For example, for some microorganisms old cultures have higher filterability, since these cultures may fragment spontaneously. Typically, fragment size may be determined by direct microscopic observation or by evaluating the filterability.

FIG. 3 shows a typical culture after filtering. By comparing FIG. 3 with FIG. 2, it may be seen that the number of fragments below the preferred size is substantially the same as that in FIG. 2, but that those fragments above the desired size are removed. The filtrate contains mostly unbranched filaments a few microns long, presumably more than uninucleate but probably containing less than about ten nuclei per colony forming unit.

In monitoring the method of the invention, it is preferable to first microscopically examine the starting population, perhaps counting the filaments, to determine what the nature of the initial population is. After fragmenting, the population should then be re-examined and, if not too different in appearance, the experiment should be abandoned or the population refragmented. These examinations may be conducted in a phase contrast microscope or by stain slides, or an electronic particle counter may be utilized. After separating, the centrifuged population or the population in the filtrate is then examined. (If a broken or leaky filter was used, a difference may be readily recognized in the ease in which filtering occurred.) This examination typically will determine what fraction of the fragment or cell count was separated, for example, 10%.

Cell counts or other observations for determining the extent of fragmenting do not provide information on the number of fragments which are viable. Thus, at certain times it may be desirable to obtain a viable count of the separated colony-forming units. This may be accomplished by plating out on an agar medium using a standard examination procedure. This will provide information as to the number of live fragments or cells, which may or may not agree with the actual count, depending upon how many survive the procedure. After experience is gained with certain microorganisms, the need for viable counts may decrease, especially where successful operating parameters can be duplicated.

The following Table I shows the results of two experiments on filter types. For convenience, these experiments were done with an untreated culture containing mainly large cells. The right-hand column gives the fraction of the culture recovered after each filtration. It may be seen that for those filters three microns and above, at least 10% of the culture passed through the Mitex and Nuclepore filters, but this was not the case with the Millipore filter. Thus, for some reason the Millipore filters did not appear suitable for this technique.

In experiment No. 2 of Table I, a complete size series was done with commercially available Nuclepore filters, as well as with five micron and ten micron Mitex filters. It may be seen that much of the culture passes through the three micron and larger filters, and a small amount of the culture (around 0.1%) passes through the 0.6 to one micron filters. Substantially nothing passes through the smaller filters, as may be expected. Thus, the 0.6 micron size appears to be the lower practical limit for the microorganism studied.

TABLE I

| | *Micromonospora* Fragmentation Viable count of filtrate | Fraction of unfiltered |
|---|---|---|
| 1. Filter | | |
| Unfiltered | $4.1 \times 10^8$ | — |
| 8 $\mu$ Millipore | $9.1 \times 10^5$ | 0.002 |
| 10 $\mu$ Mitex | $7.6 \times 10^7$ | 0.16 |
| 5 $\mu$ Nuclepore | $1.1 \times 10^8$ | 0.22 |
| 3 $\mu$ Nuclepore | $6.4 \times 10^7$ | 0.13 |
| 2. Unfiltered | $1.6 \times 10^8$ | — |
| 10 $\mu$ Mitex | $6.4 \times 10^7$ | 0.40 |
| 5 $\mu$ Mitex | $4.2 \times 10^7$ | 0.26 |
| 5 $\mu$ Nuclepore | $6.0 \times 10^7$ | 0.38 |
| 3 $\mu$ Nuclepore | $4.7 \times 10^7$ | 0.29 |
| 1 $\mu$ Nuclepore | $2.1 \times 10^5$ | 0.0013 |
| 0.8 $\mu$ Nuclepore | $2.9 \times 10^5$ | 0.0018 |
| 0.6 $\mu$ Nuclepore | $1.7 \times 10^5$ | 0.0011 |
| 0.4 $\mu$ Nuclepore | 0 (<10) | $<6 \times 10^{-8}$ |
| 0.2 $\mu$ Nuclepore | 0 (<10) | $<6 \times 10^{-8}$ |

Table II set out below provides data regarding a culture subjected to the method of the invention and under various conditions. The culture used was a two-day old Micromonospora culture and microscopic observation indicated large cells. The viable count was measured and portions were filtered through either one micron or three micron Nuclepore filters and then assayed. Portions of the culture were fragmented, either by a Virtis homogenizer or a Vortex mixer with glass homogenizing beads, both of these techniques being indicated. In the glass homogenizing beads technique, one gram of beads having a diameter of 0.2 mm were placed in a test tube 20 × 150 mm and four to six milliliters of standard undiluted culture were added. After portions of the culture were fragmented, by the indicated procedures, they were counted and filtered as before.

TABLE II

| | Young culture of *Micromonospora purpurea* (2 day) Viable count | Fraction of unfiltered |
|---|---|---|
| 1. Untreated | | |
| a. unfiltered | $1.4 \times 10^6$ | — |
| b. 3 $\mu$ | $2.8 \times 10^4$ | 0.02 |
| c. 1 $\mu$ | 0 (<10) | $<7 \times 10^{-6}$ |
| 2. Homogenized ("Virtis", speed 11, 2 min.) | | |
| a. unfiltered | $2.4 \times 10^8$ | — |
| b. 3 $\mu$ | est. $5 \times 10^7$ | 0.21 |
| c. 1 $\mu$ | $6.4 \times 10^5$ | 0.0027 |
| 3. Vortexed ("Vortex", speed 7, 2 min.) | | |
| a. unfiltered | $4.8 \times 10^7$ | — |
| b. 3 $\mu$ | $1.3 \times 10^6$ | 0.027 |
| c. 1 $\mu$ | $5.0 \times 10^2$ | $1.0 \times 10^{-5}$ |
| Increase in viable count | | |
| homogenized: | 171-fold | |
| vortexed: | 34-fold | |

The data set forth in Table II generally shows that the homogenized culture has an increased viable count and an increased filterability as compared with the untreated culture in Table I. The vortexed culture is qualitatively similar, although quantitatively less productive. Microscopic observations were in general agreement with the FIGS. 1 through 3 in that the untreated culture showed tangled networks many microns in size whereas the filtrates were mostly unbranched filaments a few microns long.

With respect to some older cultures of some strains, for example, ten-day old *Micromonospora purpurea*, microscopic observation has indicated reduced cell size. The data set out below in Table III illustrates the relatively high filterability of some old cultures, and the low increase in viable count upon homogenization. The low homogenizability has been observed a number of times in other experiments.

TABLE III

Old culture of
*Micromonospora purpurea* (10 day)

| | Viable count | Fraction of unfiltered |
|---|---|---|
| Unfiltered | $6.9 \times 10^6$ | — |
| 3 μ Nuclepore | $2.4 \times 10^6$ | 0.35 |
| Homogenized | $1.4 \times 10^7$ | (2-fold increase) |

Table IV set out below illustrates an example of an experiment with cultures of a Micromonospora strain in suitable medium at 28°C. The cultures were allowed to grow three days until microscopic observation indicated that the cells were of reasonable size and density. The initial culture, having a viable count of $1.4 \times 10^6$, was subjected to Vortex mixing with glass beads as previously set out to produce a 10-fold increase in the viable count. Filters of one micron, 2.1 micron, and three micron pore size (Nuclepore) were used to filter the vortexed culture. The results are set out in the Table below.

TABLE IV

*Micromonospora* fragmentation

| Sample | Viable count | Cell count | Viable Count / Cell count |
|---|---|---|---|
| Vortexate | $2.6 \times 10^7$ | $2.7 \times 10^7$ | 0.96 |
| 3 μ filtrate | $2.4 \times 10^6$ | $7.1 \times 10^6$ | 0.34 |
| 2.1 μ filtrate | $3.8 \times 10^6$ | $9.6 \times 10^6$ | 0.40 |
| 1 μ filtrate | $2.2 \times 10^5$ | $2.1 \times 10^6$ | 0.10 |

The above Table shows a typical increase in the viable count due to vortexing with glass beads. As may be seen, the 2.1 micron and three micron filtrations are generally similar, with the one micron filtration yielding much less material. The latter, however, produced smaller size fragments.

Some general considerations in performing the method of the invention include the fact that large cells or colony-forming units form colonies faster than small cells. Accordingly, an untreated culture which contains a wide range of cell sizes yields colonies which are heterogeneous in time of appearance, and which are heterogeneous in size at any given time. Colonies from filtrates are much more uniform, and grow more slowly than those from untreated cultures.

Where an intermediate growth period is used between two fragmentation steps, the method of the invention virtually assures genetically pure colony-forming units. For example, fragments containing twenty nuclei, a number which is substantially higher than typical, may be subjected to mutagenesis and then an intermediate growth period. If each nucleus replicates to produce 20 nuclei, each of the resultant fragments contains 400 nuclei. Assuming that when a nucleus divides, the progeny nuclei remain next to each other in the mycelium so that the fragment is a chain of 20 groups of 20 nuclei each, further fragmentation followed by filtering to yield those fragments having 20 nuclei or less results in a high probability that each of the secondary fragments is homogeneous.

These secondary fragments or colony-forming units may then be used to grow colonies for further study. Even if such colony-forming units have as many as 20 nuclei per fragment, predominantly genetically pure cultures will result. For any given fragment size, it may be possible to determine a growth time after mutagenesis which would result in genetically pure colony-forming units.

To prevent the loss of high producing strains, it is preferable to limit the growth period. The smaller the fragment, the shorter the period needs to be in order to provide a desired percentage of genetically pure filaments. The larger the fragment size, the longer the period required to provide a given percentage of genetically pure colony-forming units. During the growth period, the various genetic types are competing on the basis of growth, that is, the culture is being enriched for the superior growers in the population. Thus, unless the superior producers in a culture also are faster growers, they will be masked after a long growth period by faster growing lower producing strains.

It is not always necessary that all nuclei in each filament or colony-forming unit at the end of the cloning process be identical. Superior production characteristics may still be detectable in a given isolate from the fact that that isolate appears to be better than the norm. If such an isolate was derived from a colony grown from a colony-forming unit having two different nuclei, one a superior producer and one a normal producer, the culture may still show up as a superior culture. Having different types of nuclei per colony-forming unit does, however, make it difficult to see small improvements, since a two-nuclei fragment having a normal nucleus and an improved nucleus 20 percent better than normal is likely to appear only 10 percent better on its first test. By subsequently plating out such cultures, the two different types of nuclei can be separated and the superior one grown up for further study.

It may therefore be seen that the invention provides a method for cloning filamentous microorganisms to provide colony-forming units in which the probability is high that all nuclei therein are genetically identical. The method of the invention may be readily carried out using commercially available apparatus and known procedures. The method may be monitored conveniently at any of a variety of points, and mutagenesis may also be introduced to the method at any of a variety of convenient points.

Various modifications of the invention in addition to those shown and described herein will become apparent to those skilled in the art from the foregoing description and accompanying illustrations. Such modifications are intended to fall within the scope of the appended claims.

What is claimed is:

1. A method for cloning filamentous microorganisms, comprising, suspending the microorganisms in liquid media, subjecting the microorganisms in suspension to a fragmentation procedure to produce a substantial increase in the number of viable filaments having less than a predetermined size, and filtering the suspension of filaments through a filter having pores of a size for which there is a likelihood of passing substantially only those filaments having less than the predetermined size, said predetermined size being selected such that colonies grown from such filaments will be predominantly genetically pure.

2. A method according to claim 1 wherein the filter used has substantially straight pores of a diameter which is between about one and two times the smallest dimension of the microorganism filaments.

3. A method according to claim 1 wherein the predetermined size is selected so that the filtered filaments are likely to have less than about ten nuclei each.

4. A method according to claim 1 wherein the fragmentation is sufficient to produce an increase in the number of filaments of at least about two-fold.

5. A method according to claim 1 wherein the fragmented filaments are allowed to grow for a predetermined period of time, and are then refragmented to produce a further increase in the number of filaments.

6. A method according to claim 1 wherein the fragmented filaments are subjected to centrifugation to remove the larger filaments from suspension prior to filtering.

7. A method according to claim 1 wherein the fragmentation is carried out utilizing a homogenizer.

8. A method according to claim 1 wherein the fragmentation is carried out by agitating the suspension with glass beads.

9. A method according to claim 1 including subjecting the fragmented filaments to mutagenesis.

10. A method for cloning filamentous microorganisms, comprising, suspending the microorganisms in liquid media, subjecting the microorganisms in suspension to a fragmentation procedure to produce a substantial increase in the number of viable filaments which are less than a predetermined size, providing growth conditions for the fragmented filaments to allow growth thereof to at least double the average size of the fragmented filaments, refragmenting the grown filaments to produce at least about a two-fold increase in the number of viable filaments less than the predetermined size, and filtering to separate from the suspension of the refragmented filaments those of such filaments having less than the predetermined size, said predetermined size being selected such that colonies grown from such filaments will be predominantly genetically pure.

* * * * *